United States Patent [19]

Ahrens

[11] 4,430,085
[45] Feb. 7, 1984

[54] SAFETY SEAL CHEST DRAINAGE UNIT WITH TIPOUGR SEAL CONTROL

[76] Inventor: Thomas S. Ahrens, 2731 Meramar Dr., St. Louis, Mo. 63129

[21] Appl. No.: 354,175

[22] Filed: Mar. 3, 1982

[51] Int. Cl.³ .............................................. A61M 1/00
[52] U.S. Cl. .................................................... 604/321
[58] Field of Search .............. 604/317, 319, 321, 322, 604/323, 324, 325, 326; 137/205

[56] References Cited

U.S. PATENT DOCUMENTS

| | | | |
|---|---|---|---|
| 4,015,603 | 4/1977 | Kurtz et al. | 604/321 |
| 4,289,158 | 9/1981 | Nehring | 137/205 |
| 4,312,351 | 1/1982 | Kurtz et al. | 604/35 |
| 4,372,336 | 2/1983 | Cornell et al. | 604/321 |

Primary Examiner—C. Fred Rosenbaum
Assistant Examiner—J. L. Kruter
Attorney, Agent, or Firm—Kalish & Gilster

[57] ABSTRACT

A tip-safe chest drainage unit provides liquid sealed chest drainage. The unit has an enclosure of unitary form constructed of synthetic resin material, defining various chambers including a liquid seal chamber, a drain fluid collection chamber, manometric chambers and various equilibration and relief chambers. A chest drainage tube extends into the seal chamber, which is configured for being normally substantially filled with liquid for submerging the end of the drain tube to provide atmospheric sealing thereof. The fluid collection chamber communicates with the seal chamber for receiving fluids via the seal chamber resulting from chest drainage through the drain tube. The equilibration chambers and various baffles in the enclosure preserve fluid content upon tipping of the unit to maintain the drain tube end submerged in fluid at all times.

10 Claims, 10 Drawing Figures

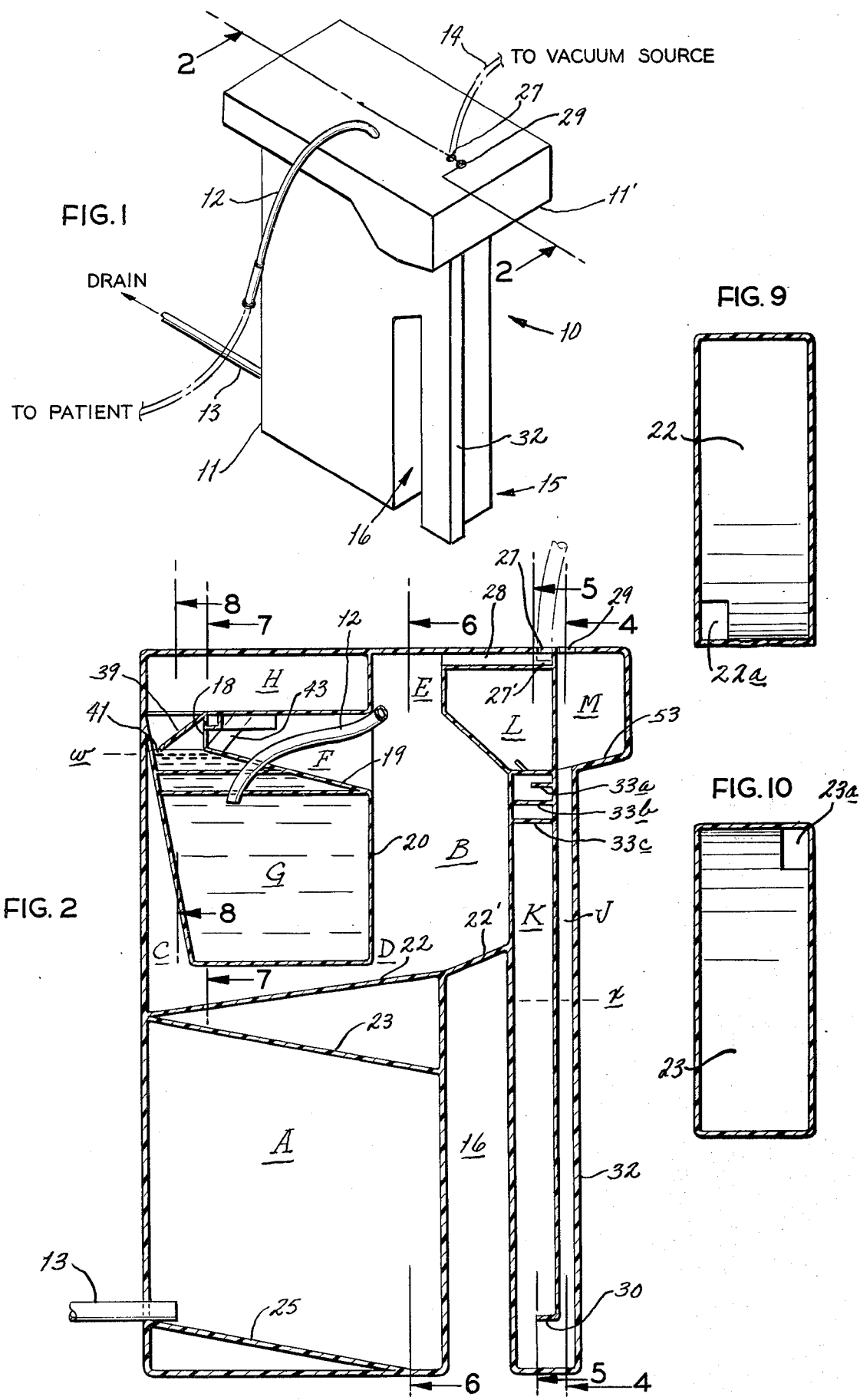

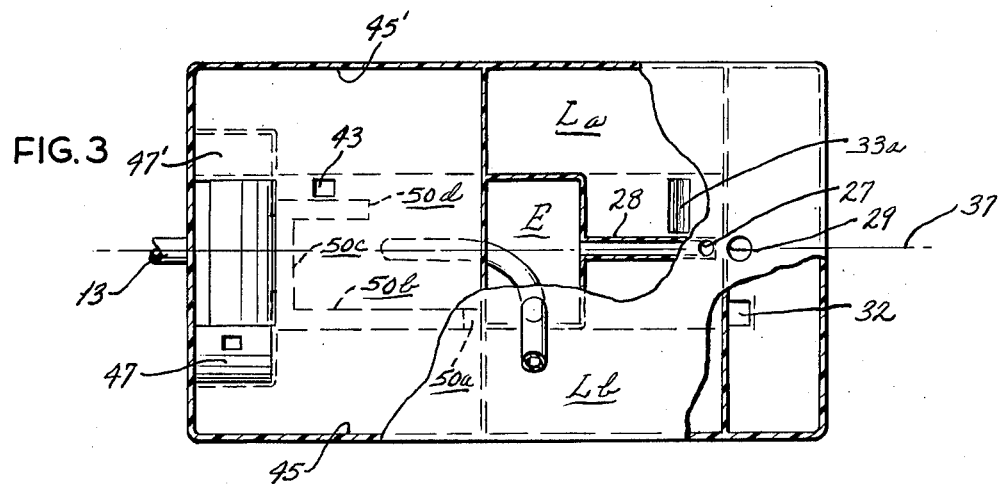
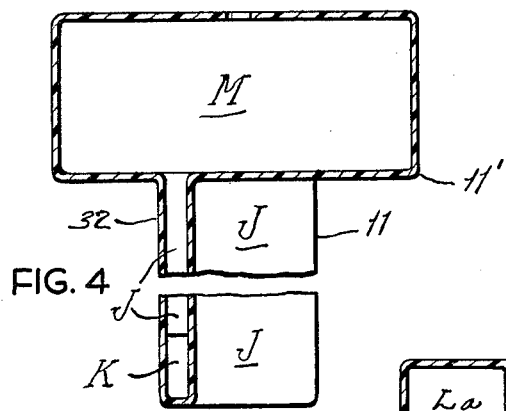
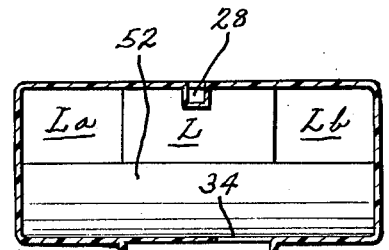
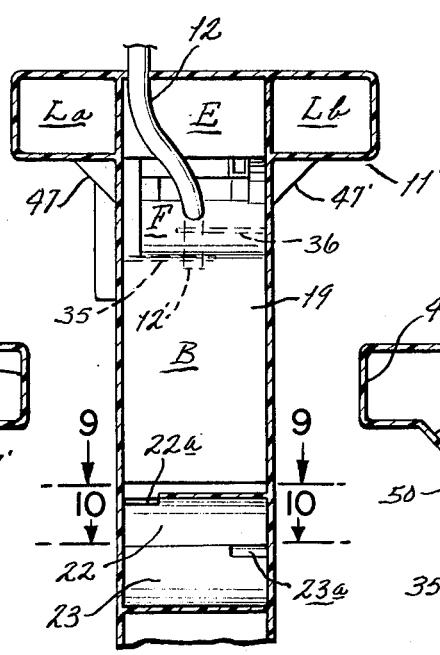
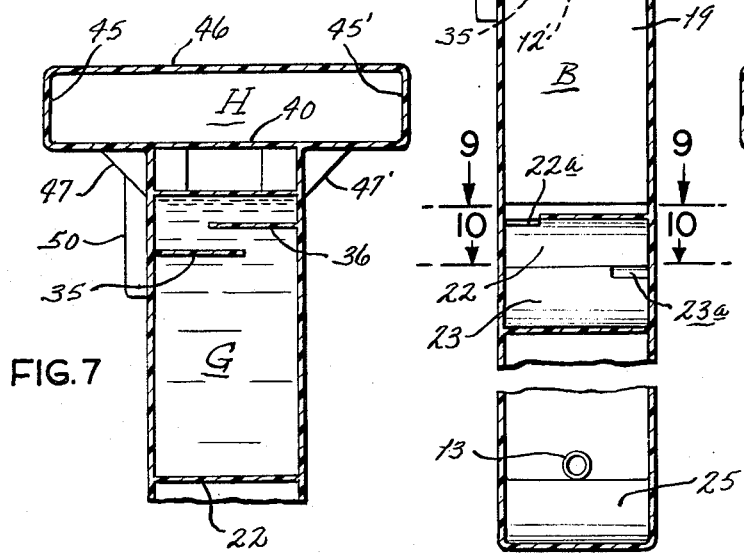
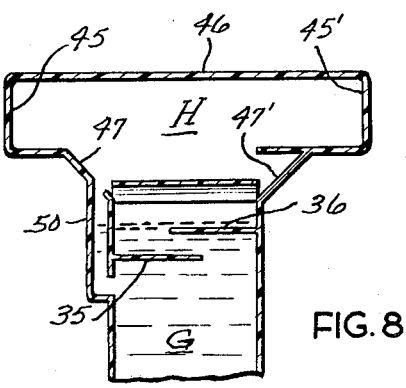

SAFETY SEAL CHEST DRAINAGE UNIT WITH TIPOVER SEAL CONTROL

BACKGROUND AND SUMMARY OF THE INVENTION

This invention relates to apparatus for the medical drainage of the pleural or thoracic cavity, i.e., what is known as chest drainage.

Chest drainage devices have long been used following chest surgery or wounds and also in the treatment of other pleural conditions requiring the fluids be drained from the pleural cavity or so-called space.

Chest drainage may be carried out with or without the application of suction but it is desirable to provide any chest drainage device with the capability of applying a negative pressure to the pleural space, i.e., aspiration, to promote drainage.

When using any type of chest drainage apparatus, extreme care must be taken to prevent the chest drain from communicating to atmospheric pressure, as this can result in lung collapse or other complications with fatal consequences. Therefore, it has been known to provide chest drainage devices with a liquid filled chamber into which the chest drain will extend so that the lower end of the drain is always under the liquid level.

Typical of arrangements having one end of the drain immersed in fluids are Kurtz et al U.S. Pat. Nos. 4,015,603 and 4,261,362, Dodge U.S. Pat. No. 4,085,751 and Tibbs U.S. Pat. No. 3,750,962. Other approaches rely upon the application of suction to the apparatus to prevent normal atmospheric pressure from being permitted to communicate with the drain. Thus, for example, reference is made to Bidwell et al U.S. Pat. Nos. 3,363,626 and 3,363,627, Fertik et al U.S. Pat. No. 3,768,478, Schachet U.S. Pat. No. 3,861,390 and Kurtz et al U.S. Pat. No. 4,112,948 as typical of this approach. Some of these patents employ a chamber in which liquid is placed and to which is connected the chest drain.

However, an important failing of all of these prior apparatuses is that they do not adequately protect a patient if the unit is tipped over, as may readily occur in a hospital, recovery or operating room where there are many person who may kick or otherwise bump the device. The above cited Dodge patent proposes a bucket-like drainage device which is resistant to sloshing or tipping having a liquid seal chamber into which the chest drain extends and configured to at least reduce the flow of liquid from the liquid seal chamber if there is such sloshing or tipping. However, nothing protects the patient from the full application of negative pressure from a vacuum source if there is such spilling, even though the liquid seal might, under some circumstances, be preserved. Also, spillage could result in collected drainage fluid being drawn up into the suction source and, therefore, if there is any tipping, a problem always results. Furthermore, the Dodge apparatus does not include an integral provision for establishing a predetermined pressure to be applied to the drain.

Thus, none of the chest drain devices of the prior art adequately protect a patient in the event the unit is tipped or placed on any of its sides. Other problems are typical of the prior art, including impossible or difficult emptying of the collection chamber without first breaking the liquid seal. Additionally, some previous chest drain devices have used a collection chamber prior to a liquid seal and this is viewed by some medical authorities as creating an undesirable or possibly hazardous large dead air space at the point of entry of the drain into the device. Another problem of some prior art devices has been the result of multiple collection chambers which allow the collected fluid to spill from one chamber to another, not only making measurement of the collected fluid more difficult but also changing the liquid seal and varying the negative pressure which is developed in the drain during aspiration by the device.

It is an object of the present invention to provide a chest drainage unit which includes a liquid safety seal chamber for maintaining constant protection for the patient, not only assuring that the liquid safety seal will not be broken should the unit be tipped over in any direction but also allowing operation to continue even if the unit remains tipped over i.e, is tip-safe.

It is also an object of the invention to provide such a chest drainage unit which prevents contamination of the liquid seal in the event of accidental tipping and causes the level of the liquid to remain relatively constant in relation to the drain point of entry into the chamber.

A related further object of the invention is the provision of such a chest drainage unit which allows the continued level of negative pressure to be maintained in the event of tipping of the unit, regardless of direction, as well as ensuring against the possibility that a high suction pressure would be applied to the patient.

Another object of the invention is the provision of such a chest drainage unit which is emptiable during use without breaking the liquid seal permitting collected fluid to be drained from the unit during usage, as well as providing for accurate measurement of the drainage fluid collected.

It is an object of the invention to provide a liquid drainage which eliminates the large dead air space characteristic of some device of the prior art, i.e., a large air space communicating with the chest drain.

Another object of the invention is the provision of such a chest drainage unit which avoids objectionable spillage of collected drainage fluids in the event of the unit being tipped over in any direction, as well as one which avoids the spillage of fluid from one collection chamber to another.

Other objects of the invention include the provision of such a chest drainage unit which is configured for permitting normal operation to continue in the event the unit is tipped over, at least for a limited time, as well as permitting drainage operation to proceed normally when the unit is once more returned to an upright condition; the provision of such a unit which is smaller than chest drainage devices of the prior art; which is of unitary construction; which can be readily and inexpensibly molded of impact resistant synthetic resin materials; and which incorporates no moving parts or objectable valves, check mechanisms or the like.

Other objects will be in part apparent and in part pointed out hereinbelow.

BRIEF DESCRIPTION OF THE DRAWINGS

FIG. 1 is a perspective view of the new safety seal chest drainage unit, as configured in accordance with and embodying the present invention.

FIG. 2 is a vertical cross-section taken generally along line 2—2 of the new chest drainage unit.

FIG. 3 is a top plan view of the new chest drainage unit, with portions thereof being broken away for illustration.

FIG. 4 is a transverse vertical cross-section taken generally along line 4—4 of FIG. 2.

FIG. 5 is a transverse vertical cross-section taken generally along line 5—5 of FIG. 2.

FIG. 6 is a transverse vertical cross-section taken generally along line 6—6 of FIG. 2.

FIG. 7 is a transverse vertical cross-section taken generally along line 7—7 of FIG. 2.

FIG. 8 is a transverse vertical cross-section taken generally along line 8—8 of FIG. 2.

FIG. 9 is a horizontal cross-section taken generally along line 9—9 of FIG. 6.

FIG. 10 is a horizontal cross-section taken generally along line 10—10 of FIG. 6.

DESCRIPTION OF THE PREFERRED EMBODIMENT

Referring now to the drawings, there is illustrated, generally at 10, a preferred embodiment of the new tip-safe chest drainage unit of the present invention. The unit includes an enclosure 11 from which extends a flexible length of tubing 12 by which the unit may be connected to the pleural cavity or space of a person for chest drainage in accordance with known medical technique. A unit of the invention may be used also for the practice of veterinarian medicine. By use of tube 12, fluids are withdrawn from the pleural cavity and collected in unit 10.

Enclosure 11 is of one piece, unitary construction, being preferably molded of an impact resistant synthetic resin material, and is of transparent or translucent character so that the actual amount of fluid collected can be measured visually with precision as well as drained off when the capacity of unit 10 is reached.

Referring to FIG. 2, the interior of unit 10 defines a plurality of chambers A through F, any one of which is adapted for holding the fluid to be collected from the patient, depending upon the orientation of unit 10, as when tipped. However, when upstanding, unit 10 is adapted primarily to receive fluid in major collection chamber A. In the event of continued receipt of drainage fluid, the fluid may accumulate also in chambers B, C and D. Normally, however, a fluid would be withdrawn from unit 10 when chamber A reaches its capacity. For this purpose, a drain tube 13 is provided, which may be a length of flexible tubing which can be maintained in a closed position by a conventional tubing clamp. The clamp is released or opened to permit fluid to be drained out. In accordance with the invention, such drainage may take place while the new unit is in operation and without danger to the patient.

Fluid may flow into any of chambers A through F in the manner described below but these chambers collectively and individually may all be referred to as the fluid collection chambers. Additional compartments at G and H may be termed seal chambers as they are adapted to provide a liquid safety seal effectively terminating collection tube 12 in liquid to prevent it from communicating with the atmosphere which would result in patient risks or dangers hereinabove noted.

Preliminarily, it may be noted that seal chamber G is adapted to be filled with water to a level above the termination 12' of the patient drain tube 12. The water level normally is indicated at w. Thus, in normal operation of the unit, chamber H does not receive water but, if tipping, the configuration of chamber H is such that fluid from chamber G may flow into chamber H until the water level equilibrates, maintaining the end of 12' of the collection tube under the water level at all times for patient protection. For this reason, chamber H may be termed an equilibration chamber. Chamber H is formed in an enlarged head or upper portion 11' of the enclosure. Similarly, chambers B through F may be referred to as equilibration chambers for collection chamber A.

The new chest drain unit is also provided with chambers J, K, L and M and it is briefly noted that chambers J and K are adapted for being approximately filled with water to serve a manometric purpose, i.e., provide a liquid manometer to regulate the level at which a partial pressure may be developed in chest drain 12 by means of tubing 14 connected to a vacuum source, all as more fully explained hereinbelow. Within the enclosure head portion 11, chamber L provides equilibration for water in chamber K while chamber M similarly protects chamber J by providing equilibration of the water in chamber J if the unit should be tipped over.

That portion of enclosure 11 which defines chambers K and L is molded to provide a downward separate extension of the unit, referred to generally by reference numeral 15. This provides a recess 16 into which the user can insert one's fingers and grasp the apparatus by gripping extension 15. This feature offers extreme convenience in carrying or manipulating the new unit, thus facilitating also picking up the unit and tilting it, as when it is being emptied through drain 13 on the opposite side.

Unit 10 need not be equipped with a base but that is essentially unneccessary because the new unit is designed to provide protection for the patient even though it may tip either forward, backward or from side to side. In this regard, it is desirable to define the orientations of the device so as to facilitate description herein of its operation. Referring to FIG. 2, the front of the unit is deemed to be that side toward the viewer, the left side being to the left of FIG. 2 and right side, to the right of the manometric chamber extension 15. The back side is that directed away from the viewer as the unit is seen in FIG. 2.

Attention is invited to the manner in which liquid drawn from the pleural cavity is drained into the device. Note that the water level w of water in chamber G is located at or slightly below an opening 18 defined by the upper edge of a sloping upper wall of chamber G which has also side walls 20, 20' and a bottom wall 21 whereby the water in chamber G cannot otherwise escape. But, upon fluid draining in through tube 12, the level will be caused to rise above w and fluid will flow over the top surface of upper wall 19 and thence into chambers B and D spilling, in the manner of a waterfall, onto an inclined superior baffle 22 which, together with an inclined lower wall 22' of chamber B, provides a surface for the liquid to flow down to an aperture 22a in one corner of the baffle and thence onto an inclined inferior baffle 23 having a similiar aperture 23a at an opposite corner, and so into chamber A. Observe that a sloping floor 25 is provided in chamber A to facilitate the drainage of the collected fluid to drain tube 13 by a very slight tilting movement of the unit to the left. The exterior walls of chamber A, being transparent, are preferably provided with suitable indicia to provide an accurate indication of the amount of fluid collected. A nominal capacity is one liter (1,000 cc).

At 27 is designated an opening 27 by which chamber E can be vented by a passage 28, it being necessary to provide for the escape of air from the unit as fluid is collected in chamber A, displacing air within the unit. Vent 27 can be open to atmospheric pressure or, as shown, may be connected to a vacuum source through tubing 14. If the latter, an opening 27' into chamber L permits suction to be developed in chamber L as well as in the fluid collection chambers A through H, thereby assisting in the drainage of fluid from the patient through drainage tube 12. But, it is emphasized that the unit can be used without suction. If suction is to be employed, chambers J and K are partially filled with water to a level, such as that shown by the dotted line x so that negative pressure cannot be developed which will exceed the height of fluid in chamber K. Chamber M communicates to atmospheric pressure through a vent 29. If high negative pressure were developed in tube 14, liquid would be drawn down through chamber J, breaking the seal at a baffle 30 at which chamber J joins chamber K to relieve the pressure.

Baffle 30 extends half the distance across chamber K from its right wall, and extends the entire lateral depth of chamber K, i.e., from front to rear. Referring to FIG. 1, chamber J is formed by a narrow extension 32 from one side of the unit so that the horizontal cross-section of chamber J is very small to prevent rapid evaporation of the liquid in chambers J and K, as well as to minimize the amount of liquid contained in these chambers. Chambers J and K are seen to provide what is, in effect, a liquid manometer.

At the upper end of chamber K are located three baffles 33a, 33b and 33c. The superior baffle 33a extends half the distance from the right side across chamber K, and across the depth of chamber K. The intermediate baffle 33b extends from the back wall of chamber K half way across its distance. Similarly, the inferior baffle 33c extends half the distance across chamber K from its front wall. Further, the opening 34 at the top of chamber K is limited to the front of the chamber.

Baffles similarly extend across the upper end of chamber G. Thus, an inferior baffle 35 extends three-fifths of the distance from the front wall of chamber G across towards its back wall, while superior baffle 36 similarly extends three-fifths of the distance from the back wall toward the front wall of chamber G. Drain tube 12 enters the tube wall 19 of chamber G and extends through baffles 35, 36 entering chamber G at a point along the axis of lateral symmetry of the unit. This axis is designated at 37 in FIGS. 3 and 6. Accordingly, the end 12' of the drain tube is centered between the front and back walls of chamber G. An additional baffle 39, angled at 75° from horizontal, extends across one end of a floor 40 of chamber H and partially into chamber G to provide an opening 41 at the upper left of chamber G to permit flow of fluid from chamber G into chamber H in the event of the unit being tipped on its left side. Interconnecting chambers G and H is a passage or tube 43 to permit fluid to run off into chamber H from chamber 17 upon the unit being tipped on its right side and also to permit a fluid to return to chamber G when the unit is righted.

Chamber H is provided with dimensions for receiving approximately 40% of the volume of chamber G, the remainder being retained by baffles 35 and 36. Chamber H has depth well beyond the front and rear of chambers A through G, as illustrated in FIG. 8, extending the depth of the enlarged upper section 11' of the unit, having side walls 45, 45' and a horizontal upper wall 46, the lower wall being defined by floor 40 as well as two sloping wall portions 47, 47' which assist in the run-off of fluid from chamber H back into chamber G when the unit is righted after having been tipped. To provide for venting between chamber H and chamber G, a further passage 49 is provided at one side of chamber G, providing a venting to prevent fluid from being forced unnecessarily out of chambers G and H and into the collection chamber. Passage 49 may be formed by an outwardly molded extension 50 of enclosure 11.

Venting between chambers G and H is also provided by a labyrinthe passage having a first portion 50a extending down from the front right corner of the central part of chamber H and opening into chamber A, a second portion 50b extending then to the left, a third portion 50c extending then rearwardly, and a fourth portion 50d extending a short distance to the right, which thus opens into chamber F. This tortuous passage allows for the escape of air when the unit is tipped to the left, while also preventing fluid unnecessarily escaping from chambers G and H if the unit is tipped to the right.

Chambers L and M similarly extend outwardly from the unit, having the same depth as chamber H to provide an enlarged lateral extent for receiving fluid in the event of tipping of the unit, as later described. Referring to FIG. 3, chamber L has two outer portions La, Lb which extend to the front and rear of chamber E. The floor 52 slopes downwardly toward the point at which chamber L communicates with chamber K to promote return of fluid into chamber K when the unit is righted after having been tipped. Similarly, the floor 53 of chamber M is inclined downwardly toward chamber J.

The following table illustrates the typical proportioning of the various chambers to achieve objects of the invention.

| CHAMBER | VOLUME |
| --- | --- |
| A | 880 cc |
| B | 160 cc |
| C | 98 cc |
| D | 90 cc |
| E | 50 cc |
| F | 35 cc |
| G | 350 cc |
| H | 300 cc |
| J | 25 cc |
| K | 250 cc |
| L | 280 cc |
| M | 180 cc |

These volumes are illustrative only, but serve to represent the relative capacities of the chambers. It will be helpful to consider the flow of fluid within the unit when it is tipped either forward or backward, or to the left or right.

Thus, if the unit is tipped to the right, chamber B will collect drainage, since fluid will continue to enter chamber G through tube 12 and flow through opening 18 into chamber B. Should chamber A be nearly or completely full upon such tipping of the unit, baffles 22, 23 will prevent the loss of fluid from chamber A, permitting only a predetermined small amount of fluid to spill from chamber A into chamber B. The typical capacity of chamber B, such as 160 cc, permits only a small part of the fluid in chamber A to be received and, in no event, no more than 150 cc. As will be apparent, baffles 35, 36 retain a major portion of the fluid in chamber G, so that the fluid level in chamber G equilibrates while maintaining the end 12' of the drainage tube at all times under the fluid surface to protect the patient. Further, the volume of chamber B is adequate for drainage should the unit be tipped on its front or back.

In the event of the unit being tipped to the left, fluid in chamber G will flow through opening 41 and into chamber H, the volume of which is such to cause the fluid level to equilibrate with the fluid level above the end 12' of the drain tube, maintaining the patient protection seal. Upon the unit being turned upright, fluid will return to chamber G through the above noted opening but does not reach run-off passage 43. It will be observed that tipping of the unit to the right will result in some fluid from chamber G entering chamber H. Fluid can enter chamber H, upon tipping to the right, until it reaches the inlet provided by passage 43. Upon equilibration, the fluid level in chamber G remains above drain tube end 12'.

If the unit is tipped on its front or back, the enlarged upper portion provided by chambers H, L and M will cause the unit to assume a position which is less than horizontal, whereby a major portion of the fluid collected during drainage will remain in chamber A. But only a limited amount of fluid will be permitted by baffles 22, 23 to flow up into the chamber H. At all times, chamber G after tipping will retain sufficient liquid upon equilibration to maintain drain tube end 12' below the fluid level.

Protection is provided for chamber K, in the event of tipping in any direction, by chamber L, the volume of the latter being sufficient to contain the entire liquid contents of chambers J and K and yet leaving vent 27' unrestricted whereby atmospheric (or vaccum assisted) venting of the unit will be maintained at all times. Similarly, chamber M will be adequate to receive the entire liquid volume of chambers J and K if the unit is tipped to the left. Baffles 33a-33c permit only negligible escape of liquid from chamber K if the unit is tipped front or back or to the right. The volume of chamber M is at least equal to that of chamber J plus half of chamber K.

An important feature of the new unit is that chamber M is vented through opening 29 which is oriented so that, even if the unit is tipped, the fluid in chambers J and K will equilibrate in such a way as to prevent the full suction from the vacuum source from being applied to chambers A-G. In this way, the patient can never incur more than the prescribed suction determined by the normal height of the column of water in chambers J and K, only less. Therefore, the unit is fail-safe in operation, ensuring patient safety.

Although the foregoing includes a description of the best mode contemplated for carrying out the invention, various modifications are contemplated.

As various modifications could be made in the constructions herein described and illustrated without departing from the scope of the invention, it is intended that all matter contained in the foregoing description or shown in the accompanying drawings shall be interpreted as illustrative rather than limiting.

What is claimed is:

1. A tip-safe underwater chest drainage unit for providing liquid sealed chest drainage, and for providing patient-protected drainage even when tipped over, said unit comprising an enclosure of unitary form constructed of synthetic resin material, said enclosure defining within it a liquid seal chamber, a chest drainage tube extending into said seal chamber, said seal chamber being configured for being normally substantially filled with liquid for submerging the end of said tube to provide atmospheric sealing thereof, a fluid collection chamber communicating with the seal chamber for receiving fluids via the seal chamber resulting from chest drainage through the drain tube, and characterized by equilibration means in the enclosure for receiving fluid upon tipping over of the unit to maintain the drain tube end submerged in fluid at all times, including when tipped over, and to permit continued receiving of chest fluids even in a tipped-over condition of the unit, said equilibration means comprising at least a first equilibration chamber for receiving fluid from the seal chamber upon tipping over of the unit and for returning the received fluid to the liquid seal chamber upon returning of the unit from its tipped-over condition to an upright position, the drain tube end being positioned within the seal chamber for remaining below the surface of liquid in the seal chamber when fluid is received in said first equilibration chamber when the unit is tipped over.

2. A tip-safe chest drainage unit according to claim 1 and further characterized by the liquid seal chamber including a plurality of baffles for maintaining within the seal chamber in an equilibrated condition a predetermined minimum amount of fluid upon tipping over of the unit, whereby the drain tube end remains at all times below the surface of the fluid in the seal chamber.

3. A tip-safe chest drainage unit according to claim 1 and further characterized by the unit including a further chamber for receiving fluid from the collection chamber upon tipping over of the unit and for returning fluid to the collection chamber upon the unit being returned to an upright position.

4. A tip-safe chest drainage unit according to claim 3 and further characterized by the collection chamber including a plurality of baffles so arranged in mutually staggered relationship for maintaining within the collection chamber by entrapment by said baffles of a predetermined amount of fluid therein regardless of whether said unit is tipped over on one side or its other side.

5. A tip-safe chest drainage unit according to claim 3 and further characterized by said further chamber including vent means for providing venting within the unit to permit collection of drainage fluid therein, said vent being oriented for maintaining venting for both upright and tipped over conditions of the unit.

6. A tip-safe chest drainage unit according to claim 5 and further characterized by the liquid seal chamber being of smaller capacity than the fluid collection chamber and configured for being initially substantially filled to capacity with a predetermined quantity of liquid, the liquid seal chamber being located within the unit at a position above the fluid collection chamber, drainage of chest fluid into said unit causing fluid to spill normally into the fluid collection chamber, the first equilibration chamber being self-contained and located proximate to the liquid seal chamber for receiving only a predetermined portion of the fluid in the fluid seal chamber upon tipping over of the unit and for returning said predetermined fluid portion to the fluid seal chamber upon the unit to returned to an upright, normal position.

7. A tip-safe chest drainage unit according to claim 6 and further characterized by the enclosure including manometric chamber means adapted for receiving a quantity of fluid establishing a manometric column of preselected height, means for connecting a vacuum source to said unit to establish a partial pressure within said unit, means for providing atmospheric venting of the manometric column thereby to maintain within said enclosure a partial pressure limited by the manometric column equilibration chamber means for receiving the fluid within said column upon tipping over of the unit and for returning the fluid thereto upon the unit being returned to an upright position, said manometric chamber means being configured for causing the fluid therein to break the suction within said enclosure if said partial pressure is excessive thereby to provide patient protection.

8. A tip-safe underwater chest drainage unit for providing liquid sealed chest drainage and for providing patient-protected drainage even when tipped over, said unit comprising an enclosure of unitary form constructed of synthetic resin material, said enclosure defining within it a liquid seal chamber, a chest drainage tube extending into said seal chamber, said seal chamber being configured for being normally substantially filled with liquid for submerging the end of said tube to provide atmospheric sealing thereof, a fluid collection chamber communicating with the seal chamber for receiving fluids via the seal chamber resulting from chest drainage through the drain tube, and characterized by equilibration chamber means in the enclosure for receiving fluid upon tipping over of the unit to maintain the drain tube end submerged, the enclosure further comprising first and second manometric chambers communicating at their lower ends and each adapted for receiving a quantity of fluid to provide a fluid manometer column, means for providing atmospheric venting to the first of said manometric columns, and means for connecting a vacuum source to the top of the second of said manometric columns, thereby to establish a partial pressure limited by the liquid manometer columns, and means for providing communication of said partial pressure to the fluid seal and collection chambers.

9. A tip-safe chest drainage unit according to claim 8 and further characterized by manometric column equilibration chambers connected with the first and second manometric chambers for receiving fluid from the respective chambers upon tipping over of the unit and for returning the fluid to the respective chambers upon the unit being returned to an upright position.

10. A tip-safe chest drainage unit according to claim 9 and further characterized by each of the first and second manometric columns including baffle means for causing predetermined minimum volumes of fluid to be retained therein under all conditions of the unit being tipped over.

* * * * *